US006517775B1

(12) United States Patent
Wang et al.

(10) Patent No.: US 6,517,775 B1
(45) Date of Patent: Feb. 11, 2003

(54) STERILANT MONITORING ASSEMBLY AND APPARATUS AND METHOD USING SAME

(75) Inventors: Jianjun Wang, Dublin, OH (US); David A. Mondiek, Dublin, OH (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/443,768

(22) Filed: Nov. 19, 1999

Related U.S. Application Data

(63) Continuation-in-part of application No. 09/360,781, filed on Jul. 26, 1999.

(51) Int. Cl.$^7$ .................. G05B 1/00; A61L 2/00; A61L 9/00; G05D 23/00; G05D 7/00
(52) U.S. Cl. ................. 422/3; 422/28; 422/38; 422/106; 422/109; 422/116; 422/292; 422/305; 53/426; 53/432; 53/442; 141/89; 141/94
(58) Field of Search ............. 422/28, 38, 106, 422/109, 116, 292, 305; 53/426, 432, 442; 141/89, 94

(56) References Cited

U.S. PATENT DOCUMENTS

| | | | | |
|---|---|---|---|---|
| 4,235,265 A | * | 11/1980 | Feliks ............ | 141/85 |
| 4,269,068 A | * | 5/1981 | Hoshino .......... | 422/62 |
| 4,897,220 A | * | 1/1990 | Trieselt et al. ..... | 252/546 |
| 4,908,188 A | * | 3/1990 | Jefferis et al. ..... | 422/111 |
| 5,036,859 A | * | 8/1991 | Brown ............ | 128/724 |
| 5,608,156 A | | 3/1997 | Ando et al. ....... | 73/31.06 |
| 5,882,590 A | | 3/1999 | Stewart et al. ..... | 422/28 |

FOREIGN PATENT DOCUMENTS

| | | |
|---|---|---|
| DK | 19855120 | 10/1999 |
| FR | 2769366 | 9/1999 |

OTHER PUBLICATIONS

NASA Tech Briefs, vol. 14(6): 106 (Jun. 1990).
J. Dietschmann, "Hydrogen Peroxide in the Inhaled Air—Monitoring and Plant Optimization Using Sensor Technology", *450 FLÜSSIGES OBST* (Liquid Fruit), vol. 63: 450–453 (Aug., 1996) (Including translation).
"A New $H_2O_2$ Measurement and Control System", Food Marketing & Technology: 41 (Feb. 1997).
I. Taizo et al., "Application of a Newly Developed Hydrogen Peroxide Vapor Phase Sensor to HPV Sterilizer", *PDA Journal of Pharmaceutical Science & Technology*, vol. 52 (1): 13–18 (1998).

* cited by examiner

Primary Examiner—Robert J. Warden, Sr.
Assistant Examiner—Imad Soubra
(74) Attorney, Agent, or Firm—David L. Weinstein; Brian R. Woodworth (57) ABSTRACT

Sterilant monitoring assembly includes an external housing defining an inlet and an outlet, and an internal flow path extending therethrough. An internal housing is located within the external housing and substantially surrounded by the internal flow path. The internal housing defines an interior sensor chamber therein, and includes a valve arrangement to join the interior sensor chamber selectively in fluid communication with the internal flow path. Preferably, the valve arrangement of the internal housing is defined by a base portion and a cover portion moveable relative to each other between an open position and a closed position. In one embodiment, the cover portion has an open end section configured for sealing engagement with an opposing surface of the base portion when moved axially to the closed position. In another preferred embodiment, the base portion and cover portion include mating peripheral walls. The peripheral walls of the base and cover portions have corresponding passageways and openings defined therein, respectively, so as to be in alignment with each other when moved to the open position and out of alignment with each other when moved to the closed position. A sterilant sensor, and any other desired sensor, is positioned to provide output signals corresponding to detected levels of sterilant and related parameters within the interior sensor chamber.

20 Claims, 5 Drawing Sheets

STERILANT MONITORING ASSEMBLY AND APPARATUS AND METHOD USING SAME

This is a continuation-in-part application of prior application Ser. No. 09/360,781, filed Jul. 26, 1999.

FIELD OF THE INVENTION

The present invention relates generally to a sterilant monitoring assembly for monitoring sterilant concentration levels within a sterilization apparatus. More particularly the present invention is directed to a sterilant monitoring assembly having an external housing defining an internal flow path for sterilant flow therethrough, and an internal housing defining an interior sensor chamber for a sterilant sensor, wherein the interior sensor chamber of the internal housing is selectively in fluid communication with the internal flow path of the external housing.

BACKGROUND OF THE INVENTION

Aseptic processing of consumable goods, such as nutritional compounds and food products, is typically effected by separate sterilization of the contents and the containers within which the contents are packaged. Subsequent to separate sterilization, the contents are placed in the containers and sealed in a sterile environment for shipment, storage and use.

Sterilization of such containers, which may include separate closures as well, prior to contacting the desired sterilized contents can be performed efficiently by use of a sterilant such as hydrogen peroxide ($H_2O_2$) vapor. In such a process, the containers are introduced into a sterilization apparatus in which the containers are flushed with hydrogen peroxide vapor. The containers are subsequently flushed with warm air or any other fluid suitable to achieve desirably low levels of residual hydrogen peroxide. This general procedure is highly effective in achieving sterilization of the containers, and likewise can be performed on any other suitable articles that will come into contact with the desired compound.

Notwithstanding the effectiveness of hydrogen peroxide ($H_2O_2$) sterilization, accurate monitoring of $H_2O_2$ vapor concentration levels can be problematic. This is due in part to the physical and chemical property changes of hydrogen peroxide vapor under processing conditions, and further due to decomposition upon contact with surfaces of various materials within the processing area. As such, undesired deviation of hydrogen peroxide vapor concentration, and excessive decomposition, can result in loss of sterility of the containers and surrounding aseptic processing area. By contrast, hydrogen peroxide vapor is corrosive in nature, and thus excessive concentration levels can result in detrimental effects to the surrounding equipment and surfaces. Furthermore, and in accordance with government standards, low residual sterilant levels must be maintained for subsequent use of the sterilized containers.

Heretofore, hydrogen peroxide vapor detection systems have been undesirably bulky, as exemplified by conventional near infrared (NIR) analysis apparatus. Additionally, known off-line testing is typically too slow to monitor sterilant levels with sufficient accuracy. Previous arrangements have not provided "real time" monitoring throughout an aseptic processing cycle, and particularly have not been capable of monitoring hydrogen peroxide vapor concentrations within the sterilization apparatus at select locations along the sterilant supply system during actual operations.

Additionally, the detected concentration of sterilants such as hydrogen peroxide within a system generally is a function of certain environment parameters, such as temperature and relative humidity, proximate the location of measurement. Conventional sterilant detection systems typically cannot or do not account for local parameter fluctuations. However, such parameter fluctuations can substantially alter signal generation and data collection results using available sensors and equipment. It therefore is beneficial to maintain operating parameters proximate the location of such measurement as uniform as possible during data collection.

In view of the foregoing, it is desirable to monitor the concentration of a sterilant, such as hydrogen peroxide, during sterilization processing. The present invention is directed to a sterilant monitor assembly to be operatively joined to the sterilant supply of the sterilization apparatus. Substantially continuous monitoring of sterilant concentrations can be achieved as sterilant is employed by the apparatus for effecting sterilization of articles therein. Likewise, the present invention enables static testing of sterilant concentration levels and related parameters, as desired or necessary.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention is directed to a sterilization apparatus having a sterilant monitoring system particularly suited to monitor concentrations of the sterilant employed by the sterilization apparatus, such as hydrogen peroxide ($H_2O_2$) vapor. The sterilization apparatus generally includes a sterilization chamber and a sterilant supply conduit to supply a sterilant to the sterilization station for sterilization of at least one article thereat. sensor chamber is joined in fluid communication with the supply conduit at a select location to allow at least a representative portion of the sterilant from the supply conduit to flow through the sensor chamber. A sterilant sensor is positioned to provide output signals corresponding to detected levels of sterilant within the sensor chamber. Operatively coupled to the sterilant sensor is a data collection circuit to receive output signals from the sterilant sensor as collected data. In this manner, sterilant concentration levels can be monitored continuously during sterilization processing, with the monitoring system operable to provide a greater degree of correlation between the sterilant levels detected within the sensor chamber and actual concentrations of a sterilant acting upon the articles.

Particularly, the present sterilization apparatus includes an enclosure within which an article conveyor operates to move a plurality of containers or like articles along a conveyor path through the apparatus. One or more sterilization stations are located along the conveyor path. Sterilant, such as hydrogen peroxide ($H_2O_2$) vapor in the presently preferred embodiment, is supplied to each sterilization station of the apparatus through a supply conduit for sterilization the articles. For example, the sterilant can be applied in the form of a fog to the external surface of each article at one sterilization station, and injected against the internal surface of each article at a different station. Preferably, the fog applied to the external surface and the vapor injected against the internal surface are applied at different concentration levels to achieve different sterilization values as may be desired.

The sterilant monitoring system of the present invention includes a sensor chamber joined in fluid communication with the supply conduit at a select location to allow at least a portion of the sterilant from the supply conduit to flow through the sensor chamber. A sterilant sensor is positioned to provide output signals corresponding to detected levels of sterilant within the sensor chamber. In the preferred embodiment, the sterilant sensor itself includes a gas-detecting semiconductor element and a heater to elevate the temperature at the gas-detecting semiconductor element. A temperature sensor, such as a thermocouple, also may be positioned to provide output signals corresponding to the ambient temperature proximate the sterilant sensor. Depending upon the type of sensor used, these sensors may be positioned within or integral with a wall of the sensor chamber. The output signals of the temperature sensor are collected in combination with the output signals from the sterilant sensor. Similarly, other sensors to detect operating parameters, such as pressure or relative humidity, also may be provided.

A data collection circuit is operatively coupled to the sterilant sensor, and to the temperature sensor or any other sensor that is provided, to receive output signals from these sensors as collected data. The collected data is processed to provide an output corresponding to the detected levels of the sterilant in the sensor chamber. Processing can be performed by a processor chip or circuit operatively coupled with the data collection circuit at the sensor chamber. Alternatively, correlation between the output signals and the corresponding sterilant levels can be performed by a remote processor located external to the sterilization apparatus. In this manner, signals representative of the collected data are transferred via the data collection circuit by a "hard-wired" configuration to the external processor, or via a wireless transfer, such as by near infrared or radio frequency transmission, to a remote communication unit operatively connected to the external processor. Accordingly, the data collection circuit includes a signal connector, such as a data port for physical connection or a transmitter for wireless transfer, to transfer the signals representative of the collected data. The output signals from the sensor, and the corresponding sterilant concentration levels correlated by the processor, can be provided to a suitable display, printer, recording device, or the like.

An electronic memory operatively coupled to the data collection circuit can be provided to create a readable memory of the data collected during a selected time interval. This electronic memory also can be operatively coupled to the internal processor, if provided, to create a readable memory of the correlated sterilant levels as well. A circuit may also be provided as part of the data collection circuit to select conditions for data collection, in combination with a signal connector, such as a data port or receiver, to allow entry of the selected conditions for such data collection.

In accordance with another aspect of the invention, a sterilant monitoring assembly is provided to establish an isolated environment for data collection, as well as enable either continuous monitoring and data collection or static testing as desired. The sterilant monitoring assembly includes an external housing defining an inlet and an outlet, as well as an internal flow path extending therethrough for sterilant flow between the inlet and the outlet. An internal housing is located within the external housing; preferably, the internal housing is substantially surrounded by the internal flow path of the external housing. The internal housing defines an interior sensor chamber therein, and includes a valve arrangement to join the interior sensor chamber selectively in fluid communication with the internal flow path of the external housing. A sterilant sensor, and any other desired sensor of suitable construction, is positioned to provide output signals corresponding to detected levels of sterilant and related parameters within the interior sensor chamber.

Although a variety of valve arrangements can be used, the internal housing preferably includes a base portion and a cover portion moveable relative to each other between an open position and a closed position. In one embodiment, the cover portion preferably is mounted for axial movement relative the base portion, and includes an open end section configured for sealing engagement with an opposing surface of the base portion when moved to the closed position. In another preferred embodiment, the base portion includes a peripheral wall having at least one passageway defined therein, and the cover portion includes a peripheral wall configured to mate adjacent the peripheral wall of the base portion. The peripheral wall of the cover portion has an opening defined therein corresponding to the passageway in the base portion, such that the passageway and the corresponding opening are in alignment with each other when in the open position and out of alignment with each other when in the closed position. In this embodiment, the cover portion preferably is mounted for rotational movement relative the base portion.

In accordance with another illustrated embodiment, a supply manifold is joined in fluid communication with the supply conduit and includes a plurality of flow lines joined fluidly in parallel. Sterilant from the sterilant supply conduit thereby can flow through the plural flow lines respectively to the sterilization station for sterilization of a corresponding number of articles positioned thereat. The conveyor of the sterilization apparatus thus is configured to move a plurality of articles in an array corresponding to the flow lines of the supply manifold so as to allow simultaneous sterilization of a plurality of articles. To detect the sterilant concentration level at the sterilization station, a sensor chamber of the monitoring system is joined in fluid communication with the supply conduit via one of the flow lines of the supply manifold. Preferably, this sensor chamber is joined to an outermost one of the flow lines of the supply manifold; that is, at the flow line located furthest from the supply conduit and thus most likely to have the greatest flow resistance and lowest concentration level within the manifold.

The present invention further contemplates a method of sterilizing articles comprising the steps of providing a sterilization apparatus including a sterilization station and a sterilant supply conduit to supply sterilant to the sterilization station. The method further includes positioning a sterilant sensor at a select location in communication with the supply conduit to provide output signals corresponding to detected levels of the sterilant at the select location, and placing at the sterilization station at least one article to be sterilized. Sterilant is directed through the supply conduit and onto the article placed at the sterilization station, with at least a representative portion of the sterilant from the supply conduit flowing by the select location. The present method also includes the step of generating output signals from the sterilant sensor corresponding to detected levels of the sterilant at the select location.

In the preferred practice of the present method, a temperature sensor is positioned at the select location to provide output signals corresponding to the ambient temperature proximate the sterilant sensor. A data collection circuit is operatively coupled to the sterilant sensor and to the temperature sensor to receive output signals therefrom as collected data. Signals representative of these output signals can be transferred via a signal connector, such as a data port or a transmitter, to a remote communication unit operatively coupled to a processor. An electronic memory may be provided to create a readable memory of data collected during a selected time interval.

The select location for the sterilant sensor may be varied, depending upon the relevant parameters to be monitored. For example, a sensor chamber may be joined in fluid communication with the sterilant supply conduit to monitor overall sterilant concentration levels introduced to the sterilization apparatus. Hence, the generating step includes generating output signals from the sterilant sensor corresponding to the detected levels of sterilant within the sensor chamber.

Using the sterilant monitoring assembly of the present invention as previously described, which includes an external housing and an internal housing with an interior sensor chamber defined therein, the method can include either continuous monitoring or static testing. For example, if continuous monitoring or data collection is desired, the method includes generating output signals from the sterilant sensor while the valve arrangement of the internal housing is maintained in an open position to generate output signals corresponding to detected parameters in the interior sensor chamber of the internal housing. If static testing is desired, the valve arrangement of the internal housing is closed from the open position to capture a static sample of sterilant within the interior sensor chamber of the internal housing. The output signals generated by the sensor(s) therefore will correspond to detected parameters of the static sample of sterilant captured within the interior sensor chamber of the internal housing. This aspect of the invention is particularly beneficial if extended exposure of the sensors to sterilant is to be avoided.

Alternatively, or additionally, the select location may include a flow line proximate a sterilization station of the sterilization apparatus. For example, the sterilization chamber may include a supply manifold joined in fluid communication with the supply conduit, wherein the supply manifold includes a plurality of flow lines joined fluidly in parallel. Sterilant from the supply manifold thus can flow through these flow lines respectively to the sterilization station for sterilization of a corresponding number of articles positioned thereat. The select location of the positioning step of this embodiment is at one of the flow lines of the supply conduit to provide output signals corresponding to detected levels of sterilant. Preferably, the method includes joining a sensor chamber in fluid communication with an outermost one of the flow lines of the supply manifold, with the generating step including generating output signals from the sterilant sensor corresponding to the detected levels of sterilant within the sensor chamber.

Other features and advantages of the present invention will become readily apparent from the following detailed description, the accompanying drawings, and the appended claims.

The accompanying drawings, which are incorporated in and constitute part of this specification, are included to illustrate and provide a further understanding of the method and system of the invention. Together with the description, the drawings serve to explain the principles of the invention.

DETAILED DESCRIPTION OF THE PREFERRED EMBODIMENT

Reference will now be made in detail to the present preferred embodiments of the invention, examples of which are illustrated in the accompanying drawings. The method and corresponding steps of the invention will be described in conjunction with the detailed description of the system and assembly.

While the present invention is susceptible various embodiments, there is shown in the drawings and will hereinafter be described presently preferred embodiments, with the understanding that the present disclosure is to be considered as an exemplification of the invention, and is not intended to limit the invention to the specific embodiments illustrated or the theory described.

Figure 1:
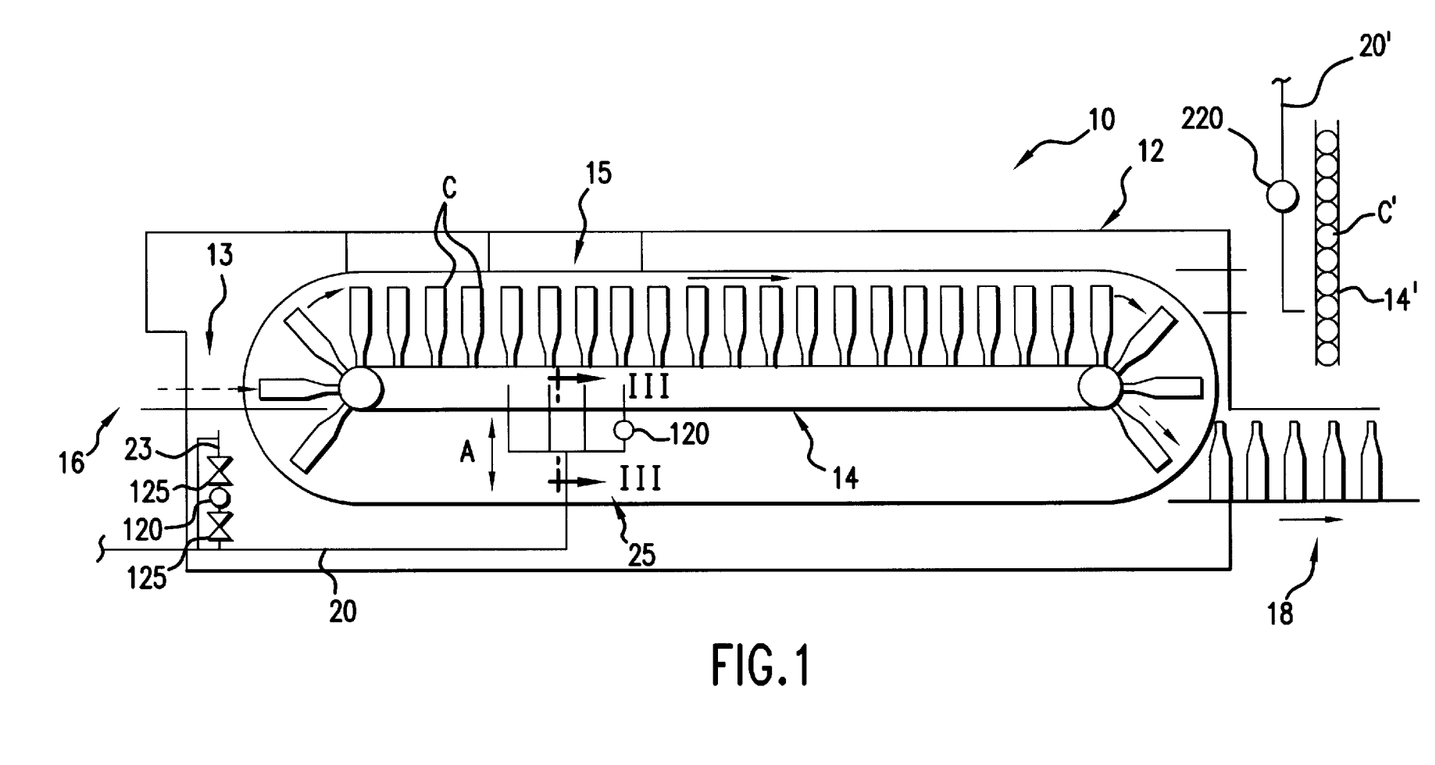
FIG. 1 is a diagrammatic side view of representative embodiment of a sterilization apparatus, including a sterilant monitoring system of the present invention.

FIG. 1 diagrammatically illustrates a sterilization apparatus 10 of the type used for effecting sterilization of containers C, such as packages, vessels or like articles. This representative sterilization apparatus 10 generally sterilizes the containers C by exposing portions of the interior and exterior of each container to a sterilant, such as hydrogen peroxide ($H_2O_2$) vapor. The containers C are processed in this fashion for subsequent filling with sterile contents, thus completing aseptic processing and packaging of the contents. The contents may include any of a variety of consumable products including, but not limited to, nutritional and therapeutic compounds, as well as food products or beverages.

The sterilization apparatus 10 itself is generally conventional in nature, and includes an enclosure 12 within which an article conveyor 14 operates for movement of containers C or other like articles to be sterilized along a conveyor path through the apparatus 10. The containers C are introduced into the apparatus at a product infeed station, generally designated by reference character 16. The containers C are received by the conveyor 14 for movement through the apparatus 10 to respective sterilization stations for processing before subsequent discharge at container discharge 18 upon completion of sterilization and filling of the processing cycle.

As the containers C are moved through the apparatus 10, both the exterior and interior of each container C is subjected to sterilizing contact with an appropriate sterilant. A variety of known sterilants are available and may be used, such as ethylene oxide, although hydrogen peroxide vapor is preferred. In the representative embodiment of the sterilization apparatus, the exterior of each container is first fogged with the sterilant at an appropriate station 13 along the conveyor path. Sterilant is supplied to the exterior fogging station via an extension 23 of a sterilant supply conduit 20 of known construction suitable for such sterilant flow.

An interior fogging sterilization station 15 also is provided, preferably downstream of station 13. Station 15 includes a supply manifold 25 having suitable probe-like flow lines 24 in fluid communication with the sterilant supply conduit. Preferably, the flow lines are moveable between an extended position and a retracted position, such that a sterilant fog can be introduced into the interior of respective containers C when the flow lines 24 are moved to the extended position, and further that the containers C can be moved along the conveyor path by the conveyor 14 for subsequent processing when the flow lines 24 are in the retracted position. As described further with regard to FIG. 3, an array of these flow lines may be provided to allow a plurality of containers C to be processed simultaneously. The sterilization apparatus 10 also may include pre-warming and drying stations along the conveyor path as needed for efficient sterilization, and effective removal of any sterilant residue prior to filling the containers C with the desired contents. The sterilization apparatus likewise can include one or more additional conveyors 14', each with corresponding sterilant supply conduit 20' and sterilization station as needed, if the containers C or like articles include additional elements, such as a closure C' or the like. Variations of such sterilization apparatus as described are available from a variety of sources, including Robert Bosch GmbH.

As previously noted, it is desirable to monitor sterilant levels within the sterilization apparatus 10. Often, however, and particularly when $H_2O_2$ vapor is used as the sterilant, monitoring can be difficult. For example, hydrogen peroxide vapor is subject to decomposition and oxidation, and thus can be difficult to monitor accurately due to its unstable and corrosive nature. While it is desirable to monitor the various stations within the apparatus 10, the hydrogen peroxide vapor itself is a very strong oxidizing agent. Furthermore, and as will be recognized, it is particularly desirable to monitor the concentration levels of sterilant as it is directed against articles as they are moved through the apparatus 10 on conveyor 14. Heretofore, however, such precise monitoring has not been possible.

Accordingly, the sterilization apparatus includes a monitoring system configured in accordance with the present invention to detect and monitor concentration levels of sterilant supplied to the apparatus and directed to the sterilization stations for sterilization of containers C or like articles. The sterilant monitoring system embodied herein, generally designated by reference character 100, includes a sensor chamber 120 joined in fluid communication with the supply conduit 20 at a select location to allow at least a portion of the sterilant from the supply conduit 20 to flow through the sensor chamber 120. Use of a sensor chamber, although not necessary for in-line applications, provides a variety of advantages. For example, the sensor chamber protects the components contained therein, as well as minimizes or eliminates condensation due to parametric conditions. Furthermore, the sensor chamber 120 also isolates the mixing effect between the sterilant and the surrounding environment when the two are exposed together, such as when the concentration level within the enclosure 12 of the apparatus 10 is different from that discharged from the container spraying nozzle 120 (e.g., $H_2O_2$ concentration is reduced due to space increase in the enclosure). The sensor chamber 120 also serves as a heat insulation/isolation jacket to prevent direct heat exchange and thus further avoid condensation there within.

The sensor chamber may be located at any of a variety of select locations along the sterilant supply system. Indeed, and as embodied herein, more than one sensor chamber 120 may be provided. The construction, shape and size of the sensor chamber 120 will depend upon the select location and the components to be housed within the chamber 120. If no sensor chamber is desired, however, a sterilant sensor may be positioned directly at a select location within the sterilant supply conduit 20 itself as will be described further below.

Figure 2:
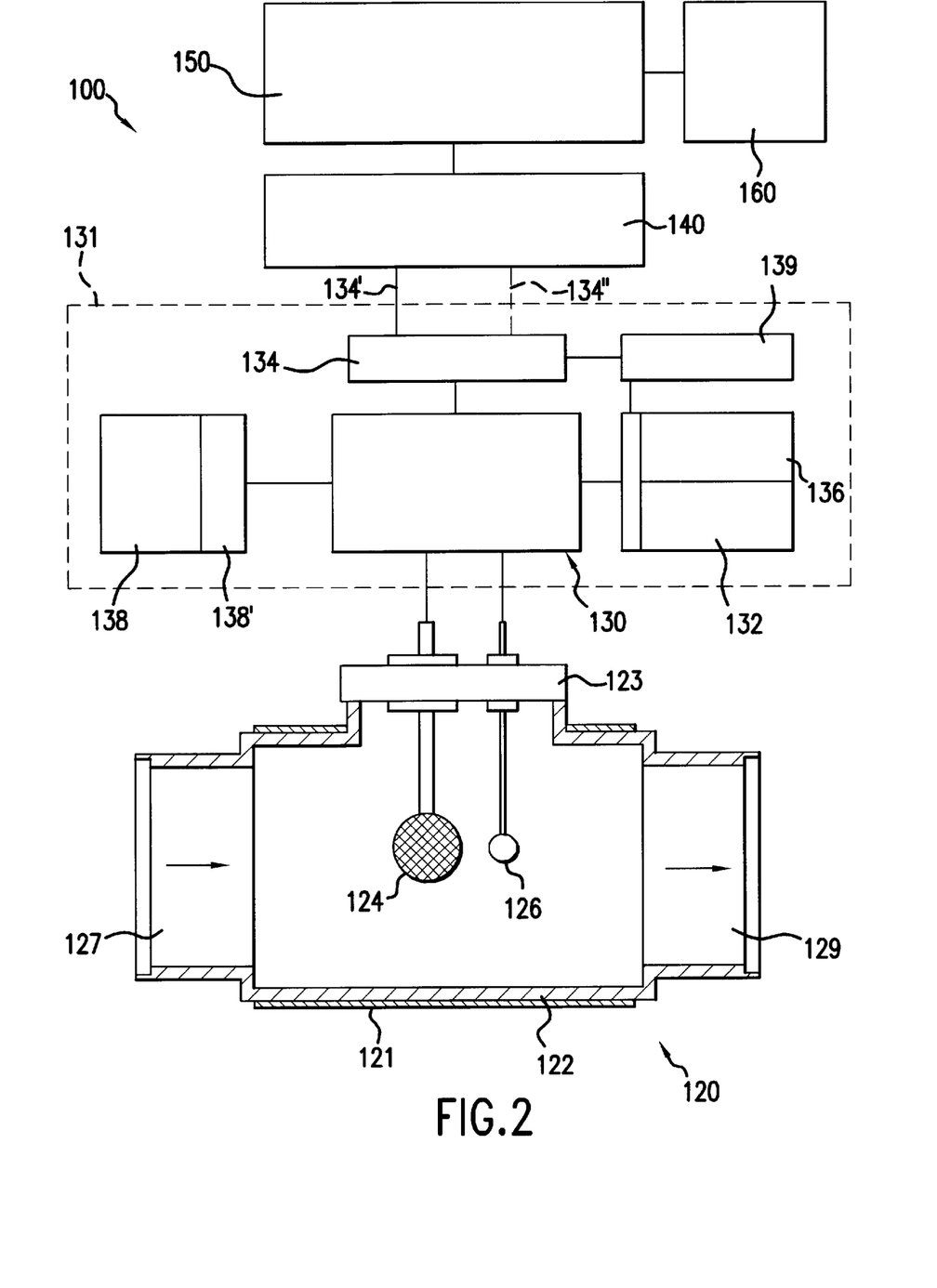
FIG. 2 is an enlarged diagrammatic view of a representative embodiment of the sterilant monitoring system of the present invention, including an "in-line" sensor chamber joined in fluid communication with a supply conduit of the sterilization apparatus of FIG. 1.

For purpose of illustration and description, and not by limitation, reference is made to FIG. 2, which shows an "in-line" sensor chamber 120 joined in fluid communication with the supply conduit 20 of the sterilization apparatus 10. The select location of this sensor chamber 120 may be proximate the inlet to the sterilization apparatus 10, or at a junction of a branch line, or simply at a location having adequate space to accommodate the sensor chamber. The sensor chamber 120 is constructed of a material capable of withstanding the operating conditions of the sterilant supply conduit 20, and includes an inlet 127 and an outlet 129 for the sterilant passing therethrough. A valve 125 may be provided, if desired, at the inlet 127 or outlet 129 of the sensor chamber 120 to control sterilant flow therethrough. In a preferred embodiment, a valve 125 is provided at both the inlet 127 and the outlet 129 to allow capture of a sterilant sample for static testing if desired. A bypass line may be provided for continued operation of station 13. Preferably, although not necessarily, an opening with a removeable cover 123 also can be provided to allow access to the components within the sensor chamber 120.

It is preferable to maintain substantially steady state conditions within the sensor chamber for enhanced detection and monitoring of the sterilant concentration levels. The sensor chamber 120 therefore is configured to isolate the influence of the surrounding environment, such as airflow, relative humidity, pressure and temperature gradients. This may be accomplished, at least in part, by constructing the sensor chamber of material having low heat transfer characteristics, such as Teflon, as well as by providing suitable insulation if desired to minimize the effects within the sensor chamber 120 resulting from the surrounding environment. It also is preferred to locate the sensor chamber 120 within the enclosure 12 of the sterilization apparatus 10 to further isolate the sensor chamber. Additionally, a heater 121, such as a heating wire and film heating element, may be provided to heat the sensor chamber, if desired or necessary, to minimize or eliminate any temperature gradient between the interior of the sensor chamber 120 and the surrounding environment. This is particularly beneficial because too extreme of a temperature gradient between the interior and exterior of the chamber 120 may result in quick condensation of the sterilant at saturated gas concentration, and thus result in inaccurate measurements.

Figure 4:
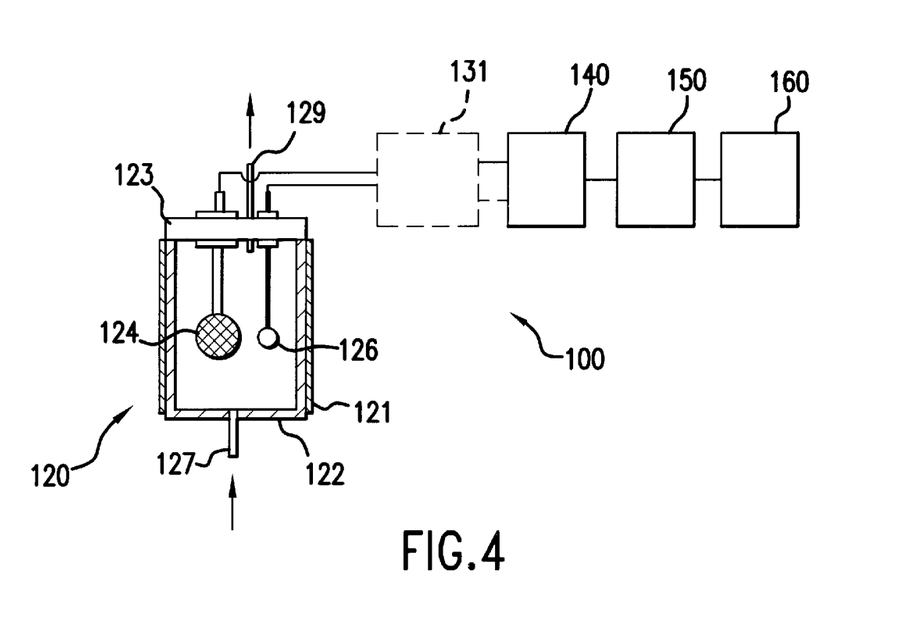
FIG. 4 is an enlarged diagrammatic view of a representative embodiment of the sterilant monitoring system of FIG. 3.

The sterilant monitoring system 100 also includes a sterilant sensor 124 to provide output signals corresponding to detected levels of the sterilant in accordance with the present invention. As embodied herein, and as shown in FIGS. 2 and 4, the sensor 124 includes a commercially available gas-detecting sensor, preferably of the type which employs a semi-conductor sensing element. This sensing element generally includes a metal dioxide (such as tin dioxide), which is sintered to form a film on the surface of an associated ceramic tube (such as alumina ceramic). A heating element, such as a resistance heating coil, is positioned within the ceramic tube to elevate the temperature of the gas-detecting semi-conductor element up to about 400° C. When the sensing element is exposed to sterilant $H_2O_2$ vapor, the metal dioxide surface absorbs the vapor molecules and causes oxidation. In this manner, it has been found that electrical resistance is reduced and, thus, the output signal generated by the sensor 124 increases proportionally with increasing vapor concentration level. In an illustrative preferred embodiment of the present sterilant monitoring assembly for use with hydrogen peroxide vapor sterilant, a Model 816 sensor from FIGARO U.S.A., Inc., of Glenview, Ill., is employed as the sterilant sensor to detect $H_2O_2$ vapor concentration levels. Alternative sensor configurations capable of performing a similar function as described likewise may be used if desired and suitable.

It also is desirable, in accordance with an additional aspect of the invention, for the sterilant monitoring system to include a temperature sensor 126, such as a thermocouple or the like, to provide output signals corresponding to the ambient temperature proximate the sterilant sensor 124. A variety of conventional temperature sensors 126 are known and may be adapted for use with the monitoring system of the present invention. A thermocouple is preferred for the present invention because temperature is expected to fluctuate within a specified window during the process. The illustrative sterilant monitoring system embodied herein, for example, includes a suitable thermocouple from Ecklund-Harrison Technologies, Inc. of Fort Myers, Fla. 33912, U.S.A. Because sterilant concentration levels are affected by the ambient temperature, the output signals from the temperature sensor 126 are used to correlate more accurately the output signals from the sterilant sensor 124 with the proper corresponding sterilant concentration levels. This function can be performed either by providing a processor chip or circuit 132 proximate the sensor chamber, if desired, or by transferring the collected data to a remotely located processor 150, as will be described. If desired, a thermister may be used in place of or in addition to the thermocouple. Furthermore, pressure, relative humidity or other parameter sensors may be provided in addition to or in place of the temperature sensor 126 to obtain corresponding parameter data respectively.

FIGS. 2 and 4 show that data collection circuit 130 is operatively coupled to the sterilant sensor 124 to receive the output signals from the sterilant sensor 124 as collected data. The data collection circuit also is operatively coupled to receive output signals from any additional sensors, if provided, such as temperature sensor 126 to provide signals corresponding to ambient temperature proximate the sterilant sensor 124. In a preferred embodiment of the invention, the data collection circuit 130 is provided simply as a conventional hard wire assembly extending from the sensor chamber 120 for connection with a remote processor as will be described. Alternatively, the data collection circuit may include a chip or printed circuit provided proximate the sensor chamber, either inside or outside, in a known manner. As described further below, and as shown, the data collection circuit 130 also may include a memory chip 132 to store entered data, a central processing unit (CPU) 136 configured to control select functions, as well as programmable solid state relays 139 for operation of the sterilant monitoring system. Preferably, these various components are provided within a housing 131 of suitable construction located proximate the sensor chamber 120.

The sterilant monitoring system of the present invention can include a hard-wired or permanent connection to a power source 138 for the electrically-driven components, such as the sterilant sensor 124 and the data collection circuit 130. In this manner, the sterilant monitoring system can be operated virtually continuously if desired. Alternatively, portable power source 138 can be provided proximate, either inside or outside, the sensor chamber 120 as part of the sterilant monitoring system for stand alone operation. Any of a variety of known portable power sources 138 may be used, such as a conventional DC lithium battery. Additionally, the power source will include a converter and/or transformer 138' as necessary to provide the appropriate power to each of the various components of the sterilant monitoring assembly 120. A light-emitting diode (LED) indicator (not shown) also can be provided to indicate activation of the power source 138. If the power source 138, and associated components, are provided proximate the sensor chamber 120, they need to be sized and housed accordingly.

An additional aspect of the invention involves the transmission of the collected data from the various sensors to a processor 150 of the sterilant monitoring system 100. FIG. 2 diagrammatically illustrates further components of the present sterilant monitoring system 100 for transfer and processing of the collected data. The sterilant monitoring system includes a remote communication unit 140 that can be operatively coupled in any of a variety of configurations with the data collection circuit 130, and further is in operative communication with the processor 150. Data transfer may be performed via a physical connection between the sterilant monitoring assembly 120 and the remote communication unit 140, or via a transmitter for wireless transmission, or both as shown in FIG. 2.

To perform data transfer via a physical connection, the data collection circuit 130 generally includes a signal connector 134, such as a conventional data port. A compatible data port is provided at the remote communication unit 140, such as the I/O port of a personal computer, to permit transfer of signals representative of the collected data from the data collection circuit 130 as shown schematically by solid line 134' in FIG. 2. This configuration is particularly applicable when the data collection circuit 130 is a conventional hard wire connection extending from the sensors. Use of this system configuration thereby allows transfer of the collected data via a physical connection to the remote communication unit 140.

Alternatively, or in addition to the transfer of collected data using a physical connector, such transfer of the collected data can be made using a conventional transmitter. The transmitter transmits signals representative of the collected data via a wireless connection, such as by radio frequency or near infrared, as shown by dotted line 134" in FIG. 2, to a receiving element of the remote communication unit 140 during the selected interval of operation. It thus can be appreciated that the sterilant monitoring system can be configured to provide "real time" transfer of collected data by either a physical connection or a wireless connection with a remote communication unit 140, thereby providing output signals representative of sterilant levels within sterilization apparatus 10 during an actual sterilization cycle.

It also is possible, in accordance with an additional aspect of the invention, to provide an electronic memory 132, such as a suitable chip or a circuit, to create a readable memory of the data collected during a selected time interval. This electronic memory 132 can be provided proximate the sensor chamber 120 or in operative communication with the remote communication unit 140. For example, a suitable electronic memory 132 for the illustrative assembly embodied herein could be incorporated using an FRB Pressure Micropack having an increased memory capacity from DATATRACE, Inc. of Lakewood, Colo., as modified to accommodate the FIGARO sensor.

The interval for data collection can be selected simply by activating a power switch (not shown) connected to the power source 138. The power switch can be located proximate the sensor chamber 120 or at the remote communication unit 140. Indeed, the selected interval can be indefinite for continuous data collection if a suitable power source is used, such as a conventional AC power outlet supply. The sterilant monitoring system 100 also may be wired in communication with the sterilization apparatus 10, such that the sterilant monitoring system 100 is activated whenever the sterilization apparatus is activated.

Alternatively, more sophisticated means may be used to select the desired interval for data collection. For example, the data collection circuit 130 may be configured to collect data during selected conditions. Such selected conditions may include start time and stop time, or detected temperature or pressure conditions at which to activate or deactivate data collection. In this manner, a signal connector, such as a physical data port or a receiver, is provided on the monitoring system 120 to receive signals from a corresponding data port or transmitter of the remote communication unit 140 to preprogram the selected conditions into the data collection circuit 130. Alternatively, it is possible for the power source to be programmed, such as by using programable relays 139 or the CPU 136, to activate the sterilant sensor 124 at a certain time prior to data collection or in accordance with a preselected schedule.

Wireless real time operations of the monitoring assembly 120 also can be accomplished, preferably by providing a near infrared or radio frequency controlled signal receiver or the like on the sterilant monitoring system 120 as part of the data collection circuit 130. In accordance with this aspect of the invention, and as embodied herein, a near infrared control system and a programmable solid state relay circuit group 139 are provided for remote power activation of the monitoring assembly 120. A variety of such control systems and relay configurations are available. The presently preferred embodiment includes a NIKON ML-3 Modulite Remote Control Set F5/N90 from B&H Photo-Video of New York as modified appropriately for operation of the sterilant monitoring system 100. For example, two transistor-transistor logic (TTL) compatible relays and a multicontact relay, each available from Philips ECG Products of Greeneville, Tenn., are used to modify this control set. A normally opened relay (RLYF71A05) is provided to activate a multicontact miniature relay (RLY5140) for heating circuit power activation to latch the heating circuit, while a normally closed relay (RLYF71B05) is used to turn off the heating power and break the latch. Because the heating current is nearly 200 mA, it is beneficial to use a relay group and optocouplers to isolate the signals. Additionally, it is preferred that the heating circuit resistance remain constant; therefore, a mechanical contact is preferred.

Data collected and transferred by the sensors and data collection circuit are processed to correlate the collected data with corresponding sterilant concentration levels. This may be performed by a processor chip or circuit 136 provided proximate the sensor chamber 120. The processor chip or circuit, if provided, is preprogrammed with the appropriate correlation using a known functional relation. This known relation can be programmed as a numeric formula, or established through the acquisition of sufficient experimental test data points at known test conditions. The processor chip or circuit is further configured to generate and transmit corresponding signals to either the electronic memory 132, if provided, or to the remote communication unit 140 as desired. The processor chip can be formed integral with the data collection circuit, or provided separately. An example of a suitable processor chip or circuit includes the EPAC™ electrically programmable analog circuit, Model No. IMP50E10C, from Digi-Key Corporation of South Thief River Falls, Minn., U.S.A. as modified accordingly, although alternatives are available.

Alternatively, or in addition to the processor chip or circuit 136, a processor 150 may be provided in operative communication with the remote communication unit 140 as illustratively represented in FIG. 2. A variety of suitable remote communication units may be used to receive the collected data. For example, if signals are to be transferred by a physical connection with the data collection circuit 130, the remote communication unit 140 may include the conventional I/O ports of a commercially available personal computer. If signals are to be transferred by wireless transmission, a suitable remote receiver may be used, such as that of the THERMO•DOT system available from Stock America, Inc. of Milwaukee, Wis. Such signals received by the remote communication unit 140 are then provided to the processor 150 to correlate the transferred signals into corresponding sterilant concentration levels using the known functional relation. Exemplary processors include any of a variety of personal computers and compatible data analysis software, such as that provided by DATATRACE, Inc. for use in conjunction with its sensors as modified to correlate the collected data with corresponding sterilant levels. Once processed, this information can be analyzed, displayed, printed, or otherwise used as desired, by peripheral equipment as designated generally by 160.

As previously noted, various components of the sterilant monitoring system are or may be located proximate the sensor chamber 120. For example, the sterilant sensor 124 and any other sensor that is included, such as the temperature sensor 126 in accordance with the preferred embodiment, may be positioned inside the sensor chamber 120, or be mounted outside the sensor chamber 120 and operatively extend therein. If positioned inside the sensor chamber 120, these sensors should be of suitable construction to prevent corrosion or damage thereto, or sealed within a suitable housing to prevent such damage. Additional components positioned proximate the sensor chamber may include the portable power source 138, the data collection circuit 130 and the processor chip or circuit, if provided. Specifically, these components may be positioned within the sensor chamber 120 or, as schematically shown in FIG. 2, located outside the sensor chamber 120. Regardless, it is preferred that these components are contained within a housing of suitable material to prevent damage or breakage due to their relatively delicate construction.

Figure 2A:
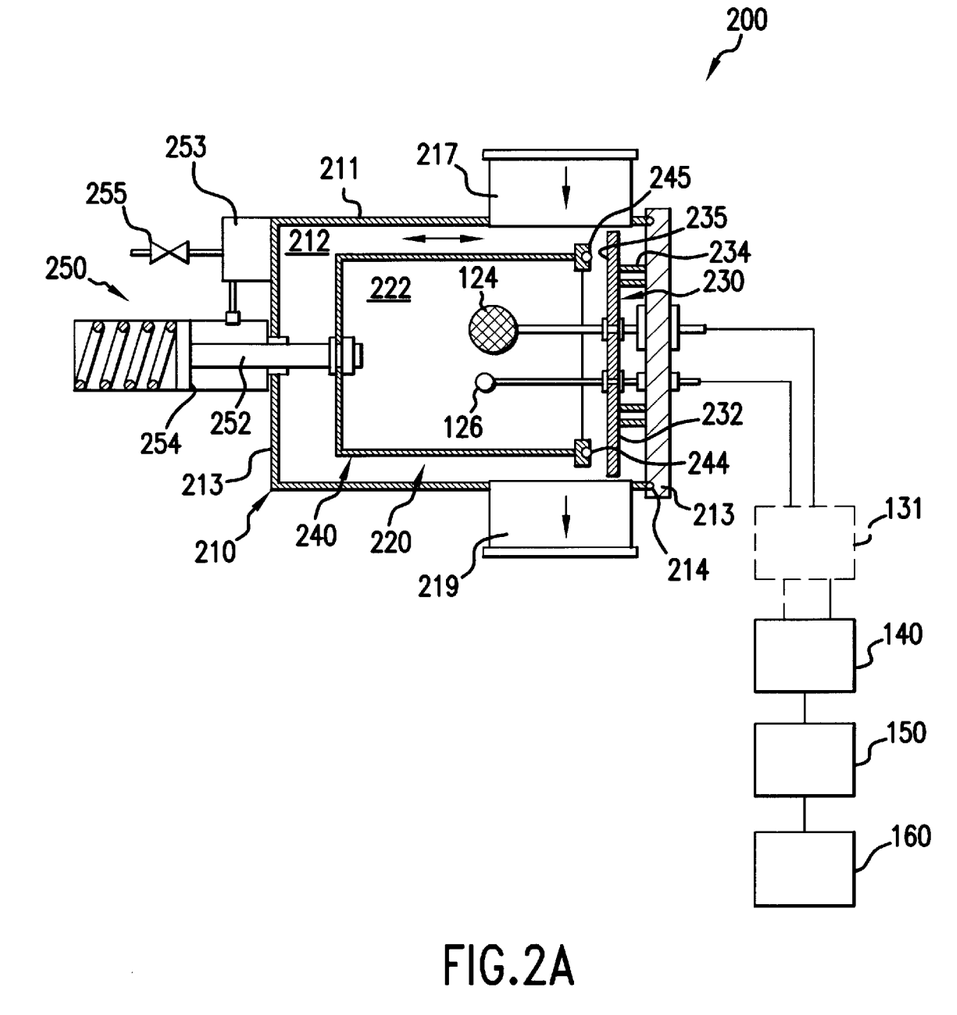
FIG. 2A is an enlarged diagrammatic view of a representative embodiment of another aspect of a sterilant monitoring assembly of the present invention, including an "in-line" sensor chamber joined in fluid communication with a supply conduit of the sterilization apparatus of FIG. 1
Figure 2B:
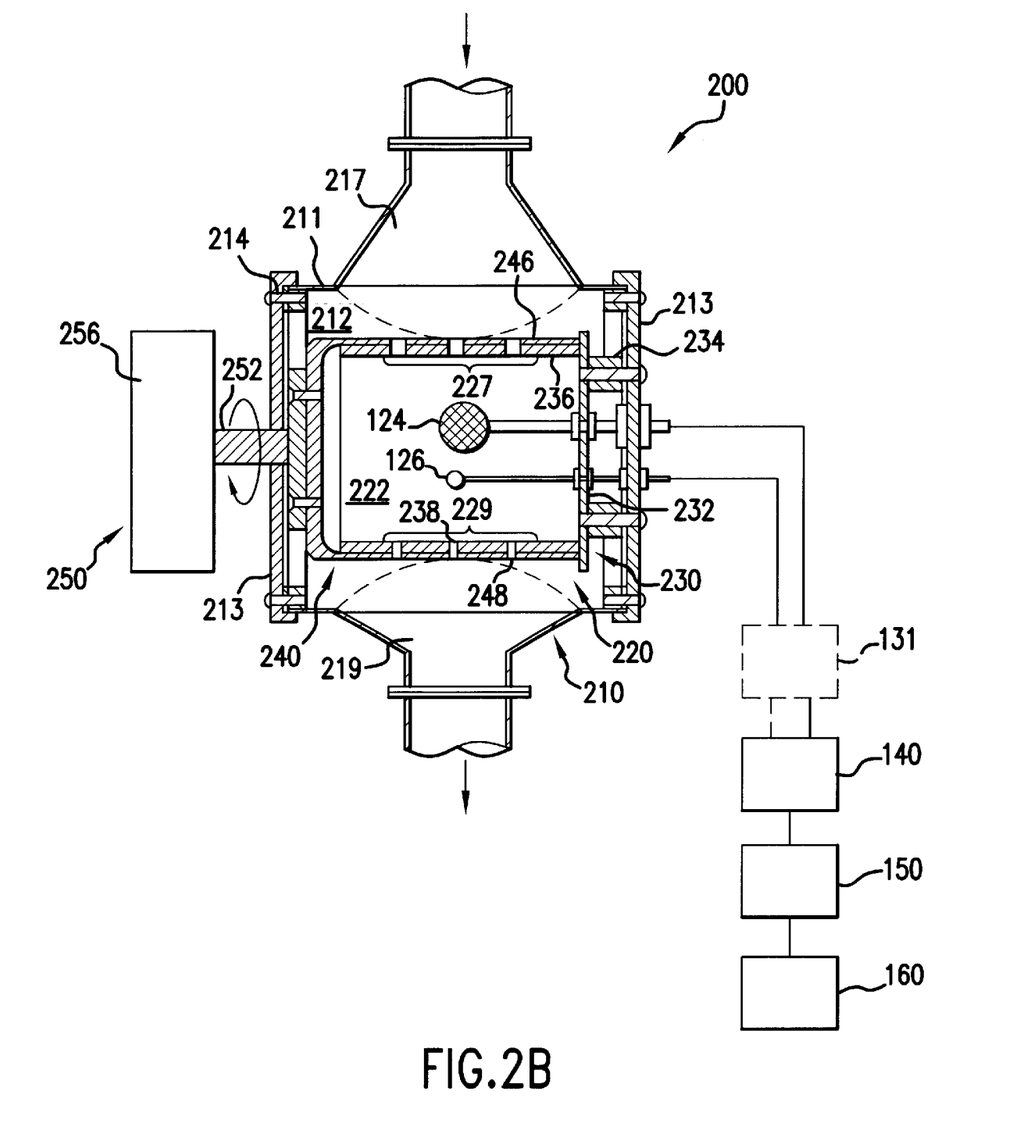
FIG. 2B is an enlarged diagrammatic view of a representative embodiment of yet another aspect of a sterilant monitoring assembly of the present invention, including an "in-line" sensor chamber joined in fluid communication with a supply conduit of the sterilization apparatus of FIG. 1

FIGS. 2A and 2B show alternative embodiments of a sterilant monitoring assembly in accordance with another aspect of the present invention. Such sterilant monitoring assemblies are capable of either continuous monitoring and data collection or static testing as desired. Furthermore, each of these sterilant monitoring assemblies is particularly suited for in-line locations that are more likely to be exposed to relatively high sterilant concentration levels. For example, certain articles, such as closures and the like, can tolerate greater exposure to sterilants due to the material of construction, the shape, or the intended use of such articles. It remains beneficial to monitor and control such exposure, however, so as to eliminate undesirable collection and waste of the sterilant. FIG. 1 shows, for purpose of illustration and not limitation, the incorporation of a sterilant monitoring assembly 200 of the present invention in fluid communication with a sterilant supply conduit 20' used for sterilization of closures C'.

Generally, and in accordance with the embodiments of this aspect of the invention, the sterilant monitoring assembly includes an external housing defining an inlet and an outlet. The external housing also defines an internal flow path therethrough, designated generally by reference character 212, for sterilant flow between the inlet and the outlet. For example, and with reference to FIGS. 2A and 2B, the external housing 210 includes a side wall 211 and opposite end walls 213 constructed of suitable material. At least one end wall 213 preferably is removable for access to the internal flow path as deemed necessary; a gasket 214 or similar seal member is provided to enhance closure of the removable end wall. Although FIGS. 2A and 2B each shows the inlet 217 and outlet 219 extending through side wall 211, any suitable configuration for sterilant flow can be used. Preferably, however, the inlet 217 and outlet 219 are in alignment with each other to minimize unnecessary turbulence and flow resistance. The inlet 217 thus can be connected in fluid communication at a select location with the sterilant supply conduit 20'; the outlet 219 can be connected in fluid communication to a desired downstream portion of the sterilant system, or opened directly to vent if desired.

Further in accordance with this aspect of the invention, and as embodied in both FIGS. 2A and 2B, the sterilant monitoring system also includes an internal housing 220 located within the external housing 210. The internal housing 220 has an interior sensor chamber 222 defined therein, and a valve arrangement to join the interior sensor chamber 222 of the internal housing 220 selectively in fluid communication with the internal flow path 212 of the external housing 210. As described further below, a sterilant sensor 124 is positioned to provide output signals corresponding to detected levels of sterilant within the interior sensor chamber 222. Additional sensors to monitor other parameters within the interior sensor chamber 222, such as temperature and relative humidity, also can be provided. In this manner, the sterilant monitoring assembly 200 can protect or shield such sensor(s) from extended exposure to sterilant, but facilitate substantially uniform environmental parameters during data collection to minimize abrupt sterilant condensation and similar detrimental phenomena.

The internal housing can be located in any desired location within the external housing. Preferably, however, and as shown in FIGS. 2A and 2B, each internal housing 220 embodied herein is located with the internal flow path 212 of the external housing 210 substantially surrounding the internal housing 220. This is accomplished by locating the internal housing 220 in a generally spaced relationship relative to the external housing 210. With the internal flow path 212 surrounding the internal housing 220, a more uniform environmental condition corresponding to that of the sterilant flow can be established about the periphery of the internal housing 220 and, thus, the interior sensor chamber 222. Furthermore, the external and internal housings are made of a suitable material, such as stainless steel or the like. More accurate measurements by the sterilant sensor 124 thereby can be obtained.

A variety of valve arrangements can be used to join the interior sensor chamber selectively in fluid communication with the internal flow path of the external housing. Although not shown, the internal housing can be provided with remotely operated control valves between the internal flow path and the interior sensor chamber. These valves would be located spaced from but in alignment with the inlet and outlet, respectively, of the external housing so as to allow sterilant to flow through the interior sensor chamber when the valves are opened, but to allow the sterilant flow to bypass around the internal housing when the valves are closed. Alternatively, splitter valves or the like may be provided to direct the sterilant flow as desired.

FIGS. 2A and 2B depict alternative valve arrangements in accordance with the present invention. The internal housing 220 of each of these embodiments includes a base portion 230 and a cover portion 240, which are mounted for relative movement therebetween to define the valve arrangement of the internal housing 220. That is, at least one portion is capable of being moved relative the other portion between an open position for sterilant flow from the internal flow path 212 to the interior sensor chamber 222 and a closed position to preclude sterilant flow from the internal flow path 212 to the interior sensor chamber 222. In the preferred embodiment, although not necessarily, the cover portion 240 is mounted for selective movement and the base portion 230 is fixed in position. If desired, the base portion 230 likewise can be mounted for selective movement, and the cover portion 240 can be either fixed or moveably mounted.

As previously noted, it is advantageous to locate the internal housing 220 such that the internal flow path 212 surrounds the internal housing 220. This is accomplished, in part, by mounting the internal housing 220 in a spaced relationship, and preferably in a substantially coaxial relationship, relative to the external housing 210. FIGS. 2A and 2B show that the base portion 230 preferably includes an isolation plate 232 spaced from an interior surface of the external housing 210 to allow sterilant flow therebetween. The isolation plate 232 is made of any suitable material, although Teflon or a substantially similar material is preferred. Spacers elements 234, also preferably made of Teflon or a similarly-suitable thermal isolating material, are used to connect the isolation plate 232 to the external housing 210 in a spaced relation using a suitable fastener. As described further below, FIGS. 2A and 2B show that the sensor(s) preferably, although not necessarily, are positioned on the isolation plate 232 of the base portion 230, which is mounted to the removable end wall 213 for easy access to the sensor(s).

With regard to the sterilant monitoring assembly of FIG. 2A, the cover portion 240 of the internal housing 220 generally is a container-shaped element having an open end section 245 configured for sealing engagement with an opposing surface 235 of the base portion 230 when in the closed position. Preferably, the open end section 245 of the cover portion 240 and the opposing surface 235 of the base portion 230 each has a planar surface configuration, although an alternative mating surface configuration can be used if desired. An O-ring, a gasket, a resilient coating or any other equivalent seal 244 can be provided to enhance sealing closure between the cover portion 240 and the base portion 230 as desired.

Relative movement between the cover portion 240 and the base portion 230 of this embodiment can be facilitated by a variety of techniques. For example, and in accordance with one preferred embodiment, the base portion 230 and the cover portion 240 can be mounted for axial movement therebetween. FIG. 2A shows the cover portion 240 mounted on a drive shaft 252 for axial movement relative to the base portion 230. Although various drive mechanisms 250 can be used to move the cover portion 240 via the drive shaft 252, the embodiment of FIG. 2A includes, for purpose of illustration and not limitation, a fluid actuation cylinder drive mechanism. As a default safety feature, the cylinder 254 preferably is biased by a spring or similar biasing means to extend the drive shaft 252 and, thus, move the cover portion 240 to its closed position. Upon actuation of the cylinder 254, such as by a solenoid valve 253 and fluid supply 255, the drive shaft 252 is retracted to move the cover portion 240 to an open position. Alternatively, the cover portion 240 and base portion 230 can be hinged for pivotal movement relative each other between the opened and closed positions. In this manner, the cover portion 240 and base portion 230 can be constructed with any of a variety of cross-sectional shapes, provided a sealed engagement can be accomplished therebetween.

FIG. 2B is directed to a sterilant monitoring assembly having a different valve arrangement in accordance with another aspect of the present invention. As shown in FIG. 2B, the base portion 230 of the internal housing 220 includes a peripheral wall 236, and the cover portion 240 of the internal housing 220 includes a peripheral wall 246 configured to mate adjacent the peripheral wall 236 of the base portion 230. Furthermore, the peripheral wall 236 of the base portion 230 has at least one passageway 238 defined therein, and the peripheral wall 246 of the cover portion 240 has an opening 248 defined therein corresponding to each passageway 238 in the base portion 230. The passageways 238 and corresponding openings 248 are located so as to be in alignment with each other to define the open position of the valve arrangement of the internal housing 220, and out of alignment with each other to define the closed position.

For example, but not by limitation, the base portion 230 and the cover portion 240 of the internal housing 220 embodied in accordance with this aspect of the invention are mounted for rotational movement therebetween. FIG. 2B shows the base portion 230 mounted in a substantially fixed position relative the external housing 210, and the cover portion 240 mounted for rotational movement relative the base portion 230. If desired, however, the base portion 230 can be rotatable instead of or in addition to the cover portion 240.

To accommodate such relative rotational movement, the peripheral wall 236, 246 of the base portion 230 and the cover portion 240, respectively, are cylindrical in shape and concentrically aligned. A mating arrangement is accomplished by forming the peripheral wall of one portion with an outer diameter substantially equivalent to the inner diameter of the other portion. For example, but not by limitation, FIG. 2B shows a base portion 230 having a peripheral wall 236 with an outer diameter substantially equivalent to the inner diameter of the peripheral wall 246 of the cover portion 240. Additional seals (not shown) can be provided between the base portion 230 and the cover portion 240 to enhance performance if desired.

A number of passageways 238 and corresponding openings 248 can be defined in the base portion 230 and cover portion 240, respectively, of the internal housing 220 as shown in FIG. 2B. Preferably, although not necessarily, a first group 227 of such passageways 238 and openings 248 are provided proximate the inlet 217 of the external housing 210 and a second group 229 of such passageways 238 and openings 248 are provided proximate the outlet 219 of the external housing 210 as shown in FIG. 2B. In this manner, sterilant introduced into the internal flow path is directed more readily through the interior sensor chamber 222 when the internal housing 220 is moved to the open position. When moved to the closed position, the sterilant flow is bypassed around the internal housing 220 from the inlet 217 to the outlet 219.

The passageways 238 and openings 248 of the internal housing 220 can be defined by any of a variety of shapes and sizes. Indeed, it is not even necessary for the size and/or shape of each passageway to be the same as that of the corresponding opening. For example, the passageways and/or openings can be regular or irregular geometric shapes, and can even extend so as to be open to an open end section of the respective peripheral wall.

In the preferred embodiment of FIG. 2B, however, both the passageways 238 and the corresponding openings 248 are spaced from the open end section of the respective peripheral wall, and are circular in shape with substantially the same diameter. Furthermore, the diameter of the passageways 238 and openings 248 in the second group 229 proximate the outlet 219 preferably is smaller than the diameter of the passageways 238 and corresponding openings 248 in the first group 227 proximate the inlet 217 to reduce flow resistance into the interior sensor chamber 222, and therefore enhance the flow characteristics of sterilant therethrough. With reference to FIG. 2B, the internal housing 220 is in the open position with each passageway aligned concentrically with its corresponding opening. The cover portion 240 therefore must be rotated a circumferential distance at least as great as the diameter of the passageway or opening, whichever is greater, to close fully the internal housing 220.

Rotational movement of the cover portion 240 relative the base portion 230 is accomplished using a drive shaft 252 operatively connected to a drive motor 256 or the like. The drive motor 256 is conventional in construction, and can be mechanical, electrical, pneumatic or hydraulic, as may be desired or practical.

Although rotational movement is preferred for the embodiment of FIG. 2B, the cover portion 240 and base portion 230 can be configured for axial movement relative to each other in accordance with the present invention. For example, and with reference to FIG. 2B, the external housing 210 can be sized to accommodate axial movement (i.e., to the right and left as shown) of the cover portion 240 therewithin. In this manner, and again with reference to FIG. 2B, the cover portion 240 would be moved an axial distance at least as great as the diameter of the passageway 238 or opening 248, whichever is greater, but preferably not as great as the spacing between adjacent passageways 238 or openings 248, to close fully the internal housing 220. If axial movement is desired, the base portion 230 and the cover portion 240 need not be cylindrical in shape, but must at least be configured to mate adjacent to each other.

As previously noted, a sterilant sensor 124 is positioned to provide output signals corresponding to detected levels of sterilant within the interior sensor chamber 222. Likewise, additional sensors, such as a temperature sensor 126 as previously described, also can be included to provide corresponding output signals representative of respective parameters within the interior sensor chamber 222. A data collection circuit 130 is operatively coupled to the sterilant sensor 124, and any other sensors provided, for communication with the remote communication unit 140 and processor 150 as previously described with regard to the embodiment of FIG. 2. In this manner, data can be collected and parameters monitored without risk of dilution or condensation, and without requiring extended exposure of the sensor(s) to the sterilant. Furthermore, one or more of the additional components previously described with regard to the embodiment of FIG. 2, such as a memory circuit 132 and a processor chip or circuit 136, can be included in the embodiments of FIGS. 2A and 2B, as schematically presented by reference character 131. Each of these components is described in detail above and need not be repeated.

Figure 3:
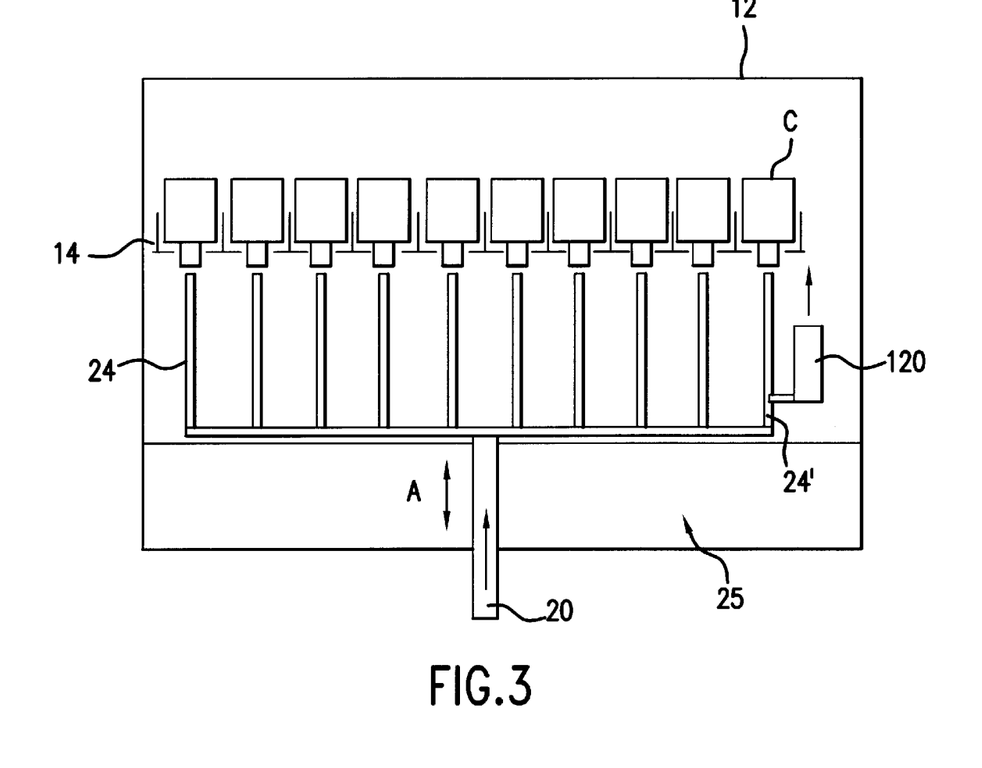
FIG. 3 is a diagrammatic end view of a sterilant supply manifold of the sterilization apparatus shown in FIG. 1, as taken along line III—III.

Reference is now made to FIG. 3, which is directed to yet an additional aspect of the sterilization apparatus and another embodiment of a sterilant monitoring system of the present invention. In this embodiment, a plurality of articles, such as containers C, are carried in an array by article conveyor 14 and moved simultaneously to the various sterilization stations of the sterilization apparatus 10, which has been microbiologically sterilized to a certain desired level. For example, and not limitation, FIG. 3 shows a conveyor 14 configured to carry ten (10) articles in a side-by-side relation, although any of a variety of different array configurations may be used.

FIG. 3 also shows a representative end view of sterilization station 15, including a supply manifold 25 joined in fluid communication with the supply conduit 20. The supply manifold 25 includes a plurality of flow lines 24 joined fluidly in parallel through which sterilant from the supply conduit 20 can flow respectively to the sterilization station 15 for sterilization of a corresponding number of articles C positioned thereat. Preferably, and as embodied herein, the number of flow lines 24 extending from the supply manifold corresponds to the array of articles C moved by the conveyor 12, such as ten (10) flow lines 24 as shown in FIG. 3. The parallel flow lines 24 of the preferred embodiment also are moveable, as shown by arrow A, between an extended position, in which each flow line is capable of introducing sterilant into the interior of a respective container C, and a retracted position to allow relative movement of the containers along the conveyor path by the conveyor. A variety of such moveable assemblies are known and available.

In accordance with the invention, a sensor chamber is joined at a select location in fluid communication with the sterilant supply conduit to detect corresponding levels of sterilant. That is, and as embodied herein, the sensor chamber 120 is joined in fluid communication with the sterilant supply conduit 20 at the supply manifold 25. The select location of the sensor chamber of this embodiment is located proximate the sterilization station 15 and, preferably, in fluid communication with one of the flow lines of the supply manifold 25, designated 24' in the illustrated embodiment.

In the preferred embodiment of the invention, the sensor chamber is joined in fluid communication with an outermost one of the flow lines 24 so as to be located furthest from the supply conduit. This location is preferred because the sterilant flow within the remaining flow lines 24 is less likely to be impacted by the flow differential, if any, generated by the sensor chamber 120. Additionally, this location is preferred because it is representative of the worst case conditions; that is, the sterilant concentration at the outermost flow line 24' is most likely to be the lowest due to flow resistance. By this configuration, detected levels of sterilant within the sensor chamber 120 at the outermost flow line 241 generally will provide an accurate, yet conservative, indication of the sterilant concentration levels of the remaining flow lines at the sterilization station. Furthermore, by locating the sensor chamber and related components as indicated, the sterilant supply system and the containers are less susceptible to contamination.

FIG. 4 is a schematic illustration of the sterilant monitoring system 100 of the present invention as used in conjunction with the manifold flow line 25. Generally, this sterilant monitoring system 100 includes the same desired features and components as described in detail with regard to that of FIG. 2. The configuration of the sensor chamber 120 is modified, however, so as to be joined in fluid communication with the outermost flow line 24' of the manifold 25. As shown in FIG. 4, the sensor chamber 120 includes an inlet 127 joined in parallel fluid communication with the flow line, and an outlet vent 129 for the ejection of sterilant therefrom. The inlet 127 and outlet vent 129 are appropriately sized to create a flow resistance substantially equivalent to that of the remaining flow lines. A flow control valve likewise may be provided on either the inlet or the outlet vent, or both if desired. By providing a valve at both the inlet 127 and the outlet 129, a sterilant sample can be captured within the sensor chamber 120 for static testing if desired. Furthermore, the outlet vent 129 can be open to atmosphere or, if desired or necessary, the outlet vent 129 can be joined in fluid communication with the supply manifold to return sterilant flow thereto if flow balance must be maintained.

As shown in FIG. 4, a sterilant sensor 124 is positioned to provide output signals corresponding to detected levels of sterilant within the sensor chamber 120, and a data collection circuit 130 is operatively coupled to the sterilant sensor 124 for communication with the remote communication unit 140 and processor 150 as previously described with regard to the embodiment of FIG. 2. In this manner, detection of concentration levels of sterilant within the interior of sensor chamber 120 provides data substantially corresponding to sterilant concentration levels within the flow lines of supply manifold 25 without risk of dilution with the enclosure air or condensation due to lower pressure at the sterilization station. Additional sensors, such as a temperature sensor 126 as previously described, also may be included to provide corresponding output signals representative of respective parameters within the sensor chamber 120. Furthermore, one or more of the additional components previously described with regard to the embodiment of FIG. 2, such as a memory circuit 132 and a processor chip or circuit 136, may be included in the embodiment of FIG. 4 as schematically presented by reference character 131. Each of these components is described in detail above and need not be repeated.

The embodiment of FIG. 4, as shown, may be used for branch line sampling as desired. Additionally, and as noted above, programmable or operable valves may be provided at the inlet 127 and outlet 129 to capture a preschedule test profile or to perform a periodic test under static conditions. In this manner, more accurate concentration levels can be detected by eliminating parametric influence, such as flow rate and pressure, if desired.

Methods of operating the present apparatus for sterilizing articles will be readily appreciated from the foregoing description. One method includes the steps of providing a sterilization apparatus such as in the form of apparatus 10, which includes a sterilization station as generally indicated at 15. A sterilant supply conduit, designated by reference character 20 in the illustrated embodiment, is provided to supply sterilant, such as hydrogen peroxide vapor, to the sterilization station 15.

The method further entails positioning a sterilant sensor 124 at a select location in communication with the supply conduit 20 to provide output signals corresponding to detected levels of sterilant at the select location. The select location may be anywhere along or in communication with, either directly or indirectly, the sterilant supply conduit 20. For example, it is preferable to position a sensor at each location wherein micro validation is desired to detect a minimum hydrogen peroxide vapor concentration level as required to reach a predetermined spore log reduction as is known in the art. Although alternative sensors may be suitable, the preferred embodiment uses a sterilant sensor having a gas-detecting semiconductor sensor 124 positioned within the sensor chamber 120 for detection of sterilant thereat.

At least one article to be sterilized, such as exemplified by container C, is placed at the sterilization station 13, 15. This may be accomplished manually, although the preferred embodiment includes an article conveyor 14 to move one or more articles into proper placement at the sterilization station 13, 15. Sterilant is directed through the supply conduit 20 and to the article C placed at the sterilization station 13, 15, with at least a portion of the sterilant from the supply conduit flowing by the select location at which sterilant levels are to be detected. In this manner, output signals from the sterilant sensor 124 are generated corresponding to detected levels of the sterilant at the select location.

The preferred method embodied herein further includes joining a sensor chamber, illustrated as sensor chamber 120, in fluid communication with the supply conduit 20 at the select location such that at least a portion of the sterilant from the supply conduit 20 flows therethrough. As will be appreciated, the step of generating output signals from the sterilant sensor 124 includes generating signals corresponding to detected levels of sterilant within the sensor chamber 120. Preferably, additional sensors are positioned at the sensor chamber to collect additional data representative of the sterilant thereat. As embodied herein, a temperature sensor 126, such as a thermocouple as previously noted, is positioned at the select location, and particularly within the sensor chamber 120, to provide output signals corresponding to the ambient temperature proximate the sterilant sensor 124.

In accordance with the invention, a data collection circuit 130 is operatively coupled to the sterilant sensor 124, and any additional sensors that may be provided, to receive output signals therefrom as collected data. The data collection circuit 130 may be a conventional physical signal connection with the remote communication unit of a processor 150. Alternatively, or additionally, the signal connector 134 of the data collection circuit 130 may include a transmitter to transmit signals representative of the collected data to a remote receiver 140. In this manner, signals representative of the collected data can be transmitted simultaneous with collection or, if the data collection circuit further includes an electronic memory 132 as previously discussed, the signals can be recorded as a readable memory and transmitted or otherwise transferred at a later time. It also is preferred that the data collection circuit 130 include a circuit to select conditions for data collection, with a signal connector provided to allow entry of such selected conditions. A remote control also may be provided for remote operation of the sterilant monitoring assembly. When the present method is practiced by use of hydrogen peroxide ($H_2O_2$) vapor as the sterilant, the sterilant sensor 124 provides an output signal corresponding to detected levels of hydrogen peroxide ($H_2O_2$) vapor.

With reference to the illustrative embodiment of FIGS. 2A and 2B, the method of monitoring concentrations of sterilant includes providing a sterilant monitoring assembly in accordance with the present invention. The sterilant monitoring assembly 200, as embodied herein, includes an external housing 210 defining an internal flow path 212 between an inlet 217 and an outlet 219, and an internal housing 220 defining an interior sensor chamber 222 within the internal flow path 212 as described in detail above. A sterilant sensor 124, as well as any other sensors as may be desired, is positioned to provide output signals corresponding to detected levels of sterilant and related parameters within the interior sensor chamber 222 of the internal housing 220.

The sterilant monitoring assembly of FIGS. 2A and 2B is connected, via the inlet 217 of the external housing 210, at a select location with the sterilant supply conduit 20' of the sterilization apparatus 10 to establish sterilant flow through the internal flow path 212 of the external housing 210. When system monitoring or data collection is desired, the method using the sterilant monitoring assembly of FIGS. 2A and 2B includes opening the valve arrangement of the internal housing 220 to join the interior sensor chamber 222 in fluid communication with the internal flow path 212 of the external housing 210 and, thus, establish sterilant flow through the interior sensor chamber 222 of the internal housing 220. The manner in which the valve arrangement is opened depends upon the valve arrangement provided, as described in detail above.

If continuous monitoring or data collection is desired, the method of using the sterilant monitoring system of FIGS. 2A and 2B further includes generating output signals from the sterilant sensor 124 while the valve arrangement of the internal housing 220 is maintained in an open position. As such, the output signals from the sensor(s) will correspond to detected parameters in the interior sensor chamber 222 of the internal housing 220. If static testing is desired, or if extreme conditions preclude extended exposure of the sensor(s) to sterilant flow from the sterilant supply conduit, then sterilant flow to the interior sensor chamber 222 can be limited by operation of the valve arrangement accordingly. That is, and prior to the step of generating output signals, the method using the sterilant monitoring system of FIGS. 2A and 2B further includes the step of closing the valve arrangement to capture a static sample of sterilant within the interior sensor chamber 222 of the internal housing 220. The output signals generated by the step of generating output signals from the sensor(s) therefore will correspond to detected conditions of the static sample of sterilant captured within the interior sensor chamber 222 of the internal housing 220 through the internal flow path 212, as generally maintained by sterilant flow surrounding the internal housing 220. If desired, an exhaust line also can be provided in fluid communication with the internal housing 220 to discharge the static sterilant sample from the internal sensor chamber 222 when data collection is completed.

In accordance with the illustrated embodiment of FIG. 4, the step of providing a sterilization apparatus includes providing a supply manifold 25 joined in fluid communication with the supply conduit 20. The supply manifold 25 includes a plurality of flow lines, 24, joined fluidly in parallel through which the sterilant from the supply manifold 25 can flow respectively to the sterilization station for sterilization of a corresponding number of articles C positioned thereat. The select location at which the sterilant sensor 124 is positioned is at one of the flow lines 24' to provide output signals corresponding to detected levels of the sterilant at the select location of the flow line. Preferably, and as previously noted, the sensor chamber 120 is joined in fluid communication with an outermost one of the flow lines 24' of the supply manifold 25, with the step of generating output signals including generating output signals from the sterilant sensor 124 which correspond to detected levels of sterilant within the sensor chamber 120.

In accordance with the present invention, the method can be performed during actual processing of the articles C by the sterilization apparatus, either continuously throughout at least a portion of the sterilization cycle, or periodically as desired. Additionally, it should be understood that the data collection and monitoring steps of the method can be performed at any time before or after the sterilization processing cycle for system verification and maintenance purposes. Additional sterilant sensors also can be provided external of the sterilization apparatus to monitor environmental sterilant concentration levels if desired.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents. Furthermore, the technical descriptions provided regarding the theory of operation are for purpose of explanation and not limitation.

What is claimed is:

1. A sterilant monitoring assembly comprising:
    an external housing defining an inlet and an outlet, the external housing further defining an internal flow path therethrough for sterilant flow between the inlet and the outlet;
    an internal housing located within the external housing, the internal housing defining an interior sensor chamber therein, the internal housing including a valve arrangement to join the interior sensor chamber selectively in fluid communication with the internal flow path of the external housing, the valve arrangement capable of being operated between an open position and a closed position, the open position allowing sterilant to flow from the internal flow path to the interior sensor chamber, the closed position precluding the sterilant from flowing from the internal flow path to the interior sensor chamber; and
    a sterilant sensor positioned to provide output signals corresponding to detected levels of sterilant within the interior sensor chamber.

2. A sterilant monitoring assembly in accordance with claim 1, wherein the internal housing is located with the internal flow path of the external housing substantially surrounding the internal housing.

3. A sterilant monitoring assembly in accordance with claim 1, wherein the internal housing includes a base portion and a cover portion, the base portion and the cover portion mounted for relative movement therebetween to define the valve arrangement of the internal housing, at least one portion capable of being moved relative the other portion between the open position and the closed position.

4. A sterilant monitoring assembly in accordance with claim 3, wherein the base portion includes an isolation plate spaced from an interior surface of the exterior housing to allow sterilant flow therebetween.

5. A sterilant monitoring assembly in accordance with claim 3, wherein the cover portion has an open end section configured for sealing engagement with an opposing surface of the base portion when in the closed position.

6. A sterilant monitoring assembly in accordance with claim 5, wherein the base portion and the cover portion are mounted for axial movement therebetween.

7. A sterilant monitoring assembly in accordance with claim 3, wherein the base portion includes a peripheral wall having at least one passageway defined therein, and further wherein the cover portion includes a peripheral wall configured to mate adjacent the peripheral wall of the base portion, the peripheral wall of the cover portion having an opening defined therein corresponding to the passageway in the base portion, the passageway and the corresponding opening being in alignment with each other when in the open position and out of alignment with each other when in the closed position.

8. A sterilant monitoring assembly in accordance with claim 7, wherein the base portion and the cover portion are mounted for rotational movement therebetween.

9. A sterilant monitoring assembly in accordance with claim 1, wherein the sterilant sensor is provided on the base portion of the internal housing.

10. A sterilant monitoring assembly in accordance with claim 1, wherein the sterilant sensor includes a gas-detecting semiconductor element and a heater to elevate the temperature of the semiconductor gas-detecting element.

11. A sterilant monitoring assembly in accordance with claim 1, wherein the sterilant sensor provides output signals corresponding to detected levels of hydrogen peroxide vapor.

12. A sterilant monitoring assembly in accordance with claim 1, further comprising a temperature sensor positioned to provide output signals corresponding to detected temperature within the interior sensor chamber.

13. A sterilant monitoring assembly in accordance with claim 1, further comprising a data collection circuit operatively coupled to the sterilant sensor to receive output signals from the sterilant sensor as collected data.

14. A sterilant monitoring assembly in accordance with claim 13, wherein the data collection circuit includes an electronic memory to create a readable memory of the data collected during a selected time interval, and a signal connector to allow transfer of signals representative of the collected data from said electronic memory to a remote communication unit in communication with the signal connector.

15. A sterilant monitoring assembly in accordance with claim 13, wherein the data collection circuit includes a transmitter to transmit signals representative of the collected data to a remote communication unit.

16. A sterilization apparatus comprising:
    a sterilant supply conduit to supply a sterilant to a sterilization station for sterilization of at least one article; and
    a sterilant monitoring assembly joined in fluid communication with the sterilant supply conduit, the sterilant monitoring assembly including
    an external housing defining an inlet and an outlet, the external housing further defining an internal flow path therethrough for sterilant flow between the inlet and the outlet,
    an internal housing located within the external housing, the internal housing defining an interior sensor chamber therein, the internal housing including a valve arrangement to join the interior sensor chamber selectively in fluid communication with the internal flow path of the external housing, the valve arrangement capable of being operated between an open position and a closed position, the open position allowing sterilant to flow from the internal flow path to the interior sensor chamber, the closed position precluding the sterilant from flowing from the internal flow path to the interior sensor chamber; and
    a sterilant sensor positioned to provide output signals corresponding to detected levels of sterilant within the interior sensor chamber.

17. A sterilization apparatus in accordance with claim 16, wherein the internal housing of the sterilant monitoring assembly includes a base portion and a cover portion, the base portion and the cover portion mounted for relative movement therebetween to define the valve arrangement of the internal housing, at least one portion capable of being moved relative the other portion between the open position and the closed position.

18. A sterilization apparatus in accordance with claim 17, wherein the base portion of the sterilant monitoring assembly includes an isolation plate spaced from an interior surface of the exterior housing to allow sterilant flow therebetween.

19. A method of monitoring concentrations of a sterilant flowing through an apparatus, said method comprising the steps of:

provi­ding a sterilant monitoring assembly including an external housing defining an inlet and an outlet, the external housing further defining an internal flow path therethrough for sterilant flow between the inlet and the outlet, an internal housing located within the external housing, the internal housing defining an interior sensor chamber therein, the internal housing including a valve arrangement to join the interior sensor chamber selectively in fluid communication with the internal flow path of the external housing, the valve arrangement capable of being operated between an open position and a closed position, the open position allowing sterilant to flow from the internal flow path to the interior sensor chamber, the closed position precluding the sterilant from flowing from the internal flow path to the interior sensor chamber, and a sterilant sensor positioned to provide output signals corresponding to detected levels of sterilant within the interior sensor chamber;

connecting the inlet of the external housing in fluid communication at a select location wit h a sterilant supply conduit of the sterilization apparatus to establish sterilant flow through the internal flow path of the external housing;

opening the valve arrangement to join the interior sensor chamber in fluid communication with the internal flow path of the external housing to establish sterilant flow through the interior sensor chamber of the internal housing; and generating output signals from the sterilant sensor corresponding to detected levels of the sterilant in the interior sensor chamber of the internal housing.

20. A method of monitoring concentrations of a sterilant flowing through an apparatus in accordance with claim 19, wherein prior to the step of generating output signals, the method further comprises the step of:

closing the valve arrangement to capture a static sample of sterilant within the interior sensor chamber of the internal housing; the output signals generated by the step of generating output signals from the sterilant sensor corresponding to detected levels of the static sample of sterilant captured within the interior sensor chamber of the internal housing.

* * * * *